United States Patent [19]

Womack, II et al.

[11] Patent Number: 5,092,988

[45] Date of Patent: Mar. 3, 1992

[54] SYSTEM FOR MONITORING INJECTION WATER QUALITY USING FILTRATION, PRESSURE REGULATION AND MASS MEASURING

[75] Inventors: Irving F. Womack, II, Placentia; Mitchell F. Peterson, Diamond Bar, both of Calif.

[73] Assignee: Chevron Research Company, San Francisco, Calif.

[21] Appl. No.: 595,525

[22] Filed: Oct. 11, 1990

[51] Int. Cl.$^5$ .............................................. B01D 36/00
[52] U.S. Cl. ................................. 210/85; 73/61.1 R; 73/863.23; 73/864.34; 73/864.73; 177/4; 177/210 R; 210/90; 210/137; 210/248; 210/258; 210/540
[58] Field of Search .......... 73/61.1 R, 863.01, 863.21, 73/863.23, 864.34, 864.73; 177/4, 25.14, 210 R; 210/90, 137, 248, 257.1, 258, 259, 513, 537, 540; 417/474; 137/590, 590.5, 513.85; 166/266, 268

[56] References Cited

U.S. PATENT DOCUMENTS

| | | | |
|---|---|---|---|
| 3,386,585 | 6/1968 | Weyand et al. | 210/445 |
| 3,638,476 | 2/1972 | Paterson et al. | 73/61.1 R |
| 3,924,449 | 12/1975 | Moreau et al. | 73/61.1 R |
| 4,689,989 | 9/1987 | Aslesen et al. | 73/61.1 R |
| 4,836,017 | 6/1989 | Bozek | 73/61.1 R |

OTHER PUBLICATIONS

"Methods for Determining Water Quality for Subsurface Injection Using Membrane Filters", National Association of Corrosion Engineers, NACE Standard TM-01-73 (1976 Revision), printed in 1984 by (NACE).

Primary Examiner—Robert A. Dawson
Assistant Examiner—Joseph Drodge
Attorney, Agent, or Firm—Edward J. Keeling

[57] ABSTRACT

An apparatus for testing water quality for subsurface injection that provides for samples of infinite volume to be passed over a membrane filter at a constant pressure. The apparatus uses a positive displacement pump drawing suction on the water source and discharging to a membrane filter. Between the pump discharge and the filter is an oil/water separation vessel to allow for sampling of well production fluids before oil removal if necessary. Fitted to the oil separation vessel is an adjustable pressure regulator, also known as a back pressure regulator, for maintaining constant pressure over the filter. The filter discharge water is collected in a volume calibrated vessel. The vessel is connected to load cells, and a data collection device records weight as a function of time. By measuring the water density, a time/volume curve can be automatically plotted by the data collection device. This apparatus would find application in performing a variety of field tests, however, testing of water quality for injection wells is the most likely application for the apparatus.

6 Claims, 1 Drawing Sheet

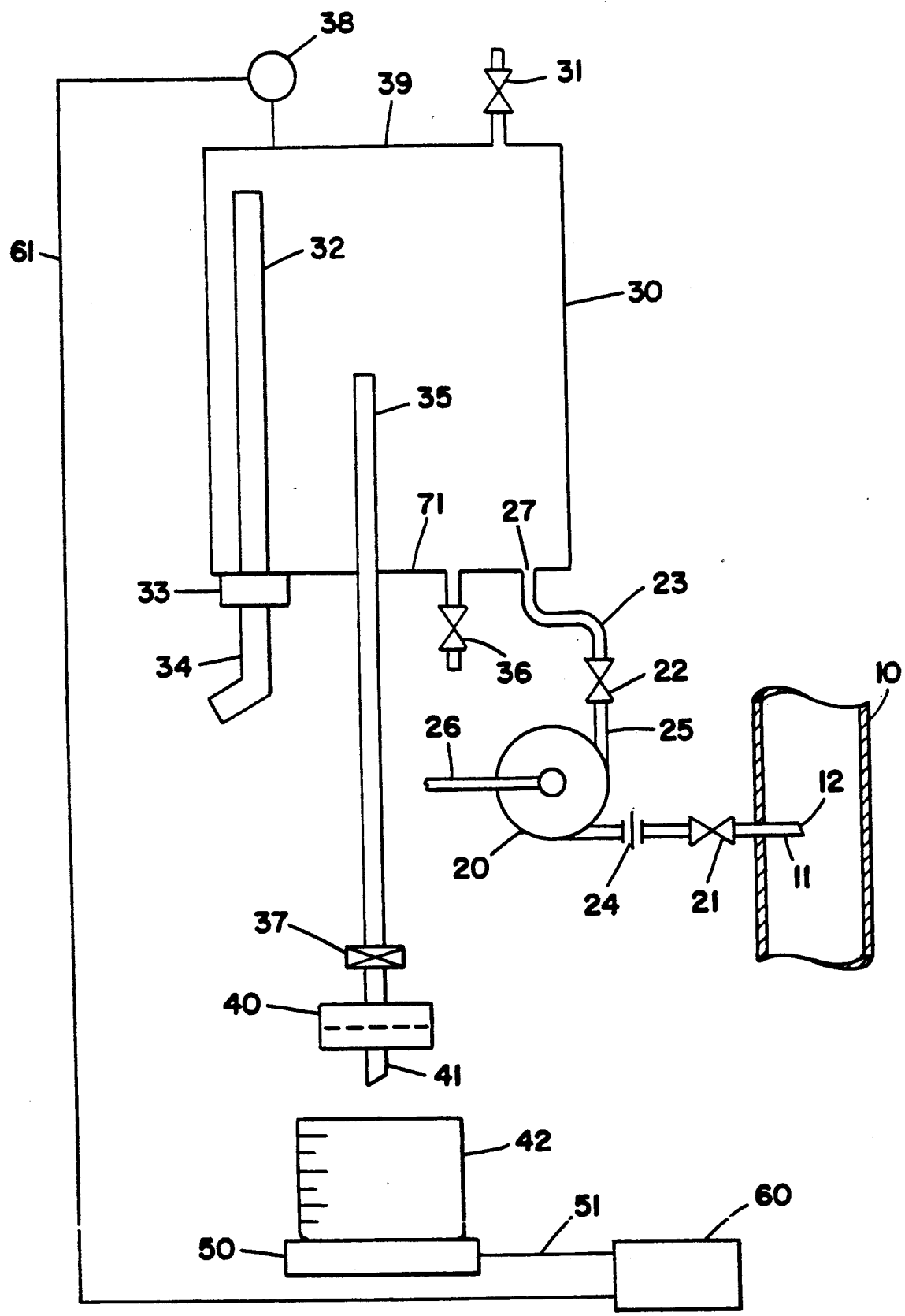
FIG_1

SYSTEM FOR MONITORING INJECTION WATER QUALITY USING FILTRATION, PRESSURE REGULATION AND MASS MEASURING

BACKGROUND OF THE INVENTION

The present invention relates to the area of evaluating water quality for subsurface injection.

The present invention relates to the field of determining water quality for subsurface injection using membrane filters, following the title of the NACE standard Methods for Determining Water Quality for Subsurface Injection Using Membrane Filters, National Association of Corrosion Engineers, NACE Standard TM0173-84 (1976 Revision), hereinafter referred to as TM0173-84. This test is relevant in oil production fields where fluids produced from the wells typically contain large portions of water (for example, water-to-oil ratios of 10:1 are not uncommon). Disposal of the water has always been a problem, and standard practice has been to reinject the water back into the ground via a separate injection well. This practice has the added benefit of acting as a drive fluid to push more oil to the producing well. However, it is important to know some properties of the injected water since the injection practice may in fact damage the well. Standard TM0173-84 has been developed to provide information regarding some of these properties to operators in the field.

Specifically, TM0173-84 outlines two (2) tests. Quoting from TM0173-84, Section 3, page 1:

3.1 Rate v. Cumulative Volume Test
- 3.1.1 This test method consists of passing a fixed volume of injection water through a membrane filter under constant pressure and measuring the flow rate and cumulative volume of water at intervals.
- 3.1.2 This test is primarily designed for monitoring injection water quality. A plot of the flow rate vs. cumulative volume of water gives a general indication of the injected water.

3.2 Suspended Solids Test
- 3.2.1 This test method consists of collecting samples of primary solids (as defined in Section 2.1.1 of TM0173-84) as they exist in a water system. The suspended solids from several liters of water are collected on a membrane filter in a manner that permits larger, more representative samples than those obtained from bottle samples.

3.3 The suspended solids test and the rate volume test can be run concurrently.

Section 6 of TM0173-84, "Test Conditions," states:
- 6.3.1 The test pressure for rate vs. cumulative volume should be 20 psig (138 kPa)±10% at the membrane. Because permeability variations can occur with pressure-sensitive filter cakes, it is advisable to determine if a test conducted at higher constant pressure is more definitive of the effective water quality in the system. (Emphasis added).
- 6.3.2 Test pressure is obtained by suitable mechanical devices for on-stream sampling and by a pressure regulator between the nitrogen source and the sample reservoir for pressurized tests.

6.4 Sample Volume
- 6.4.1 For routine rate vs. cumulative volume tests, the sample size shall be 2.5 L (liters). Where water quality permits rapid filtration, samples up to 10 L or more may be required for meaningful interpretation. (Emphasis added).

FIG. 2 of TM0173-84 discloses an apparatus for providing a sample of infinite volume, if required, as suggested in Section 6.4.1, above. However, the only mechanism for controlling pressure on the membrane filter as required in Section 6.3.1 is the manual valve at the sample source. Manual control of pressure requires attention each time the test is run to assure the initial pressure is correct and to monitor the pressure to guarantee that unacceptable variations (±10%, per Section 6.3.1, above) do not occur. These pressure variations are possible if the pressure in the sample manifold in the apparatus in TM0173-84 FIG. 1 varies. Manual control may not be quick enough to adjust for pressure variation, and depending on the type of valve used at the sample point, precision of control may be unacceptable. Summarizing, manual control of the pressure over the membrane can be both labor intensive and inaccurate. A better means of controlling the required constant pressure in an infinite volume sample apparatus is needed.

FIG. 3 of TM0173-84 discloses an apparatus for maintaining constant pressure over the membrane by applying a pressure source such as compressed nitrogen gas. This apparatus has some inherent drawbacks. First, if a higher pressure is desired, as suggested it might in TM0173-84 Section 6.3.1, some means of controlling the pressure over the membrane is needed. While no means is disclosed in the FIGURE shown, it is conceded that means known to the art could be employed, such as putting an adjustable pressure controller on the nitrogen supply line, or putting an adjustable pressure relief device on the calibrated reservoir. A further constraint of this apparatus is that it is volume limited. This creates two problems. First, if a larger sample is desired, as suggested by Section 6.4.1, a larger reservoir may be needed. Thus, the apparatus must be constructed with the maximum volume anticipated in mind, or, retrofits at time and expense may be required. Second, if during a test it is determined that a larger volume is in fact needed, the test must be aborted and run again with the larger volume. This will result in a time intensive trial-and-error method to optimize the volume desired. The volume limited sample reservoir also introduces the chance for the reservoir to empty and nitrogen gas to blow directly through the membrane. This may damage the membrane and would at least make any test results highly suspect. Consequently, constant attention to the apparatus is required. Summarizing, again the apparatus disclosed in FIG. 3 of TM0173-84 is both labor intensive and subject to error. A better method of accommodating sample volumes in a constant pressure test apparatus is needed.

Sometimes a modified sample of the injection water is desired. Standard practice in the oil field is to extract oil (and gas) from the fluids extracted from the formation and then inject the produced water back into the formation to act as a drive mechanism to enhance oil recover. This injected water is the water that is the subject of the test in TM0173-84. However, if the water is sampled before the oil is removed, it is not a representative sample of the injected water. Sometimes it is not practical to sample the water after oil removal. If this is the case, then an "oily" sample must be drawn, decanted, the oil removed, and then tested. But produced water contains many chemicals which may react with oxygen (for example, free iron) but don't because the production-extraction-injection process is a closed process. Therefore, the decanted sample must be kept in an oxygen free atmosphere. This is technically not difficult, but is a great inconvenience for the operator running the test, particularly in the oil field. Thus what is needed is an apparatus that will allow on line sampling of produced water before oil is extracted.

SUMMARY OF THE INVENTION

The claimed invention overcomes three problems inherent in current methods for running the National Association of Corrosion Engineers, water quality test TM0173-84. These three problems were discussed in the BACKGROUND section of this application. Summarizing, what is needed to overcome these three problems is:

1. The need for an infinite volume sample apparatus that will allow simple, reliable constant pressure control;
2. The need for a constant pressure sample apparatus that will allow infinite volume samples;
3. The need for a sample apparatus that will allow samples of well production fluids to be taken before the oil is extracted from the sample, yet will be representative of the de-oiled water injected into the well.

The present invention overcomes the constant pressure control problem by use of a positive displacement pump coupled with an adjustable pressure regulation device on the discharge of the pump. The pump is located between the infinite sample source and the membrane filter. The infinite sample source would typically be either the subsurface water injection manifold or the manifold carrying fluids produced from the well. The present invention also overcomes the second problem in that it results in a constant pressure sample apparatus, by virtue of the pump and back pressure regulator, that allows infinite volume samples by virtue of the pump's connection to the sample source. The present invention overcomes the third problem by incorporating a water-oil separation chamber after the pump discharge but before the membrane filter. Further advantages of the claimed invention will become apparent in the detailed description that follows.

BRIEF DESCRIPTION OF THE FIGURE

In order to facilitate the understanding of this invention, reference will now be made to the appended drawing of the preferred embodiment of the present invention.

FIG. 1 is a drawing of the preferred embodiment of the present invention.

DETAILED DESCRIPTION OF THE PREFERRED EMBODIMENTS

In its broadest form the invention provides apparatus for testing water quality of subsurface injection water, specifically for testing in accordance with National Association of Corrosion Engineers test method TM0173-84.

The apparatus has a positive displacement pump drawing a suction of the source of the sample. This sample source is typically a pipe manifold in an oil field which contains either fluids produced directly from the well or the de-oiled groundwater to be reinjected back into the well. The use of the positive displacement pump provides several advantages:

1. First, by drawing a sample directly from the pipe manifold, a sample of any volume can be taken. This potentially reduces the equipment required for tests of varying volumes, but more importantly, it allows for the duration of the test to be extended if a decision is made during the running of the test that the original sample size was too small in volume.
2. A positive displacement pump will isolate the test apparatus from pressure variations in the manifold from which the sample is being drawn, and can compensate for inadequate pressure in the manifold. That is, if the manifold pressure is below the required test pressure, the pump can make up this difference. A positive displacement pump is best suited to achieve this function as its discharge pressure is independent of the suction pressure, unlike say a centrifugal pump.
3. A positive displacement pump is preferred over a centrifugal pump, as the former is not as disruptive to the sample as is the latter. This is important since agitation of the sample can disrupt certain chemical properties (e.g., supersaturation of chemicals) thus resulting in a nonrepresentative sample.

The pump discharges to a separation/dampening vessel. The function of this vessel is twofold:

1. First, the vessel acts as a separation chamber for the removal of free oil from the sample. This is a desirable aspect if a de-oiled sample cannot be obtained. While the test is to be run on de-oiled water, that is, the kind of water reinjected into the well, sometimes it is not possible to sample de-oiled water. Thus an apparatus that can sample at either point, i.e., before or after de-oiling, has wider application.
2. Second, the vessel acts as a dampening means to reduce the small cyclic pressure variations inherent in a positive displacement pump. This is an important feature as the test must be run under constant pressure conditions at the filter. Since the filter is connected to the vessel, and the vessel to the positive displacement pump, unless some means of dampening the pump's pressure oscillations is employed, the filter will be subjected to those same variations.

The vessel is fitted with a means for regulating the pressure in the vessel. This in turn regulates the fluid pressure at the membrane filter, since the filter is connected to the vessel as described below. Any of several means for regulating the pressure in the vessel can be employed. The present invention uses a liquid pressure relief valve, also known as a back pressure regulator, with a manually adjustable setpoint. This relief valve is preferably mounted on the bottom of the vessel and is connected to an internal overflow line. The overflow line serves two purposes. First, as an outlet for excess fluid, which is one and the same as pressure control in a system employing a positive displacement pump. Second, the overflow line acts as a draw for the separated oil to be removed from the vessel.

The vessel is fitted with a bottom outlet which leads to the filter holding means. This invention does not address any changes to the filter holding means, and any of several means available on the market can be employed. Preferably, the filter holder is a device capable of sustaining high pressures. Desired parameters of the preferred filter holder are discussed further, below, in the detailed description of FIG. 1.

The outlet from the filter leads to a sample collection vessel mounted on a mass measuring means, more commonly known as a scale, balance, mass balance, etc.

This balance is preferably an electronic balance having a continuous electronic output of the reading at any given time. This output can be connected to an electronic means for recording data. The parameters recorded would include time, the balance output, and a correlation of the two by means of an internal clock. The data recording means could be expanded to include a data manipulation means with output display capabilities, either electronic, graphic on paper, data on paper, or any other common data output not to be limited by the examples mentioned. Further details of the preferred data collecting and processing means are discussed below in the detailed description of FIG. 1.

Turning now to the embodiment shown in FIG. 1, the fluid to be sampled flows in manifold 10, which can be either a main well production fluid pipe, a well water injection pipe, or any sample source in which the desired fluid to be sampled flows. There is no typical or common point at which these samples are drawn. This manifold is fitted with a permanent sample inlet tube 11 which penetrates into the manifold a sufficient distance to collect a representative sample of the fluid. The open end of the sample inlet tube is typically cut at 45° to reduce the undesirable effects that occur when fluids flow past an open pipe at 90° to the pipe. The location and characteristics of the sample inlet tube are well known in the art, and optimizing the design of this component can easily be accomplished by anyone skilled in art. The sample inlet tube can be isolated by the sample inlet tube block valve 21. This valve is typically a stainless steel globe valve which is commonly available on the market. The sample inlet tube block valve is connected to the sample coupling 24. This coupling can be any of the common means employed in the art for connecting pumps to tubing. In the preferred embodiment, the coupling is a screwed fitting.

The sample pump 20 is connected to the sample coupling 24. The sample pump is preferably a positive displacement pump, and more preferably a peristaltic tube pump. In the preferred embodiment a Masterflex (registered trademark) ST-07021-26 pump was used with an output of up to 1000 ml/min and a maximum output pressure of 40 psig. The peristaltic pump is preferred since it minimizes disruption of the sampled fluid and can be constructed of nonreactive fluid contacting components such as Tygon F-4040-A (Tygon is a registered trademark). The pump is powered by power source 26, which in the preferred embodiment is 12V DC electric power. The sample pump discharge 25 is connected to the separation vessel 30 by the connection tube 23. Between tube 23 and sample pump discharge 25 is sample pump isolation valve 22, whose purpose is to allow the rest of the apparatus to be isolated from the sample pump 20 for service or other needs.

The sample discharged from the sample pump 20 enters the bottom of the separation vessel at sample inlet 27. The sample vessel is preferably a cylindrical tube fabricated of a clear material to allow an operator to observe the test and monitor the oil/water interface. In the preferred embodiment the separation vessel is fabricated of 2.5" diameter LEXAN tubing (Lexan is a registered trademark of General Electric Corp.) with ⅜" thick walls and having a flat top 39 and bottom 71 of Lexan also ⅜". The bottom 71 is glued to the Lexan tubing and the top 39 is secured by screws and sealed with an O-ring in the preferred embodiment. While the vessel described is the preferred embodiment, any vessel which is made of nonreactive materials and of sufficient strength to withstand the maximum anticipated operating pressures can be used. The volume of the separation vessel should be large enough to allow a resonance time of on the order of magnitude of between 2 and 30 minutes. The separation vessel is fitted with a vent valve 31 affixed to the top 39. The vent valve is used to vent air from the separation vessel to the atmosphere before starting the test. Venting assures that no oxygen will contact the sample water rendering the sample nonrepresentative. A pressure indicator 38 is also attached to the top 39 of the separation vessel. This pressure indicator is used to monitor the pressure of the test. The pressure indicator should have a range sufficient to accommodate the possible range of test pressures. The pressure indicator can be a visual gauge, however, in the preferred embodiment the indicator is a pressure transducer which sends a signal to the data collection device 60 via the conduit 61. Affixed to the bottom 71 of the separation vessel is a drain valve 36 whose purpose is to allow the separation vessel to be emptied after and between tests. The drain valve 36 can either be routed to discharge to a drain or any other convenient and proper disposal source for the sample water.

Mounted internally to the separation vessel is the overflow tube 32. This tube penetrates an opening at the bottom 71 of the separation vessel and is tightly sealed around this opening so that the only route for surplus fluid to exit the separation vessel during normal operation is by flowing down and out of the overflow tube. In the preferred embodiment of the experiment the overflow tube is a ⅜" nominal diameter tube of Lexan (a registered trademark of General Electric Corp.). The overflow tube should extend vertically up into the separation vessel until it is within near proximity of the top 39. The distance from the top is not critical but should be sufficient to allow free flow out of the overflow tube without lowering the liquid level in the separation vessel to the point where normal operation of the test is disrupted. In a test where the sample is taken from production fluids before they are de-oiled, oil would rise to the top of the separation vessel during the test and would flow out of the separation vessel via the overflow line. In this way an accumulation of oil in the separation vessel during the test is avoided. Accumulation of such oil would ultimately render the test results invalid.

Attached to the external portion of the overflow tube 32 where it extends from the bottom 71 of the separation vessel is the back-pressure regulator 33, "the regulator." The regulator has a manually adjustable release pressure at which the regulator 33 opens allowing sample water above the top of the overflow tube 32 to exit the separation vessel. The purpose of the regulator is to maintain the test pressure on the separation vessel. The regulator also acts to purge oil accumulating at the top of the separation vessel. If oil accumulation during the test is anticipated, the operating pressure of the sample pump 20 should be set high enough that there is occasional need for the regulator to open, thus purging the accumulated oil from the separation vessel. The range of the regulator should be sufficient to accommodate all anticipated test ranges. In the preferred embodiment a regulator manufactured by Testcom with a range of 0–50 psig was used. The outlet 34 from the regulator can be directed to any acceptable source for disposal or recylcing of the overflow fluid.

A second tube, the sample outlet tube 35 extends vertically up into the separation vessel. This sample outlet tube penetrates the bottom 71 of the separation vessel and is tightly sealed at the penetration. The sample outlet tube should extend about half way into the separation vessel. The top of the sample outlet tube should be sufficiently below that of the overflow tube 32 so that any accumulated oil does not enter the sample outlet tube, but sufficiently above the bottom 71 of the separation vessel so that any solids in the sample which do not stay in suspension remain on the bottom 71. The sample outlet tube should be fabricated from a non-corrosive material. In the preferred embodiment a ¼" nominal diameter Lexan (a registered trademark of General Electric Corp.) tube is used. The sample outlet tube is connected to toggle valve 37 whose function is to start and stop the flow of the sample to the filter, thus effectively starting and stopping the test. The toggle valve 37 should be a quick acting valve. The sample flows through the toggle valve and into the filter holder 40. The filter holder used in the preferred embodiment is a Geiman "2220" vented membrane filter holder. Filter holders of this type are described in U.S. Pat. No. 3,386,585 Filter Holder and Support.

The filter outlet 41 directs the filtered sample to a sample collection vessel 42, "the collection vessel." The collection vessel should be large enough to accommodate the maximum sample volume anticipated. Collection vessels of 10 liters or more would not be uncommon. The materials of construction of the collection vessel are not critical. The collection vessel rests on an electronic balance or other mass measuring means 50, for example, load cells. Mechanical mass measuring means such as a spring balance scale could also be employed. In the preferred embodiment an Ohaus model CT6000-S balance with Q-6000 gram range and an RS-232 data interface connection 51 is used.

A data recording/processing means 60 can be incorporated into the apparatus. At a minimum this data recording/processing means would record the electronic balance output (which is proportional to the mass of the sample that has passed through the filter) and the test pressure (if a pressure transducer is used as the pressure indicating means at 38) as functions of real time. This data can be recovered from the data recording device's memory and processed manually or downloaded to a data processing means and processed automatically. Alternately a combined data recording means/data processing means can be used. In the preferred embodiment a Hewlett Packard HP-41CV was used with a compatible Hewlett Packard printer. The HP-41CV is desirable since the apparatus is envisioned as primarily being used in the field. The HP-41CV makes a compact, portable, low cost data recording processing means with self contained power supply and real time capability. Other acceptable data recording/processing means include portable personal computers such as laptops form Compag and Toshiba, full size personal computers such as the IBM PS/2, or even a full mainframe computer. The output from the data processing/recording means could include any display, either graphical or in tabular form, in which any of the three measured variables, i.e., time, pressure and mass, are used either directly or in formulas or algorithms. As an example, the sample density could be measured and stored in the data processing means. This measured value could then be used along with the recorded mass to calculate the net volume of sample passed through the filter. The net volume could then be compared against time and a volume versus time curve could be plotted. The most common outputs from a data processing means would be a Rate versus Cumulative Volume curve and a Pressure Degradation versus Time curve.

From the above description it is evident that the present invention provides an apparatus for measuring water quality for subsurface injection. Although only specific embodiments of the present invention have been described in detail, the invention is not limited thereto but is meant to include all embodiments coming within the scope of the appended claims.

What is claimed is:

1. An apparatus for performing water quality tests, comprising a sample pump arranged for drawing a sample from a sample source; a separation vessel located for receiving said sample from said sample pump, said separation vessel being for oil/water separation and dampening of pressure fluctuations from said sample pump; an overflow tube extending upwards internally into said separation vessel and downwards externally from said separation vessel, said overflow tube being for removal of oil from said sample and removal of surplus sample from said separation vessel; a pressure regulator connected to said overflow tube external to said separation vessel, said pressure regulator controlling the internal pressure of said separation vessel and control of fluid from said overflow tube; a sample outlet tube extending upwards internally into and externally downwards from said separation vessel, said sample outlet tube extending upwards into said separation vessel a shorter distance than said overflow tube; a filtration means connected to a portion of said sample tube external to said separation vessel; a means for collecting said sample as said sample passes out of said filtration means; and a means for measuring mass connected to said sample collecting means, said mass measuring means being for measuring the mass of said sample as said sample passes out of said filtration means.

2. The apparatus according to claim 1 wherein said sample pump is peristaltic pump.

3. The apparatus according to claim 2 wherein said mass measuring means includes obtaining of electronic outputs.

4. The apparatus according to claim 3 further comprising:
(a) a pressure sensing means connected to said separation vessel, said pressure sensing means having an electronic output; and
(b) a data collection means for recording electronic outputs from said pressure sensing means and said mass measuring means.

5. The apparatus according to claim 4 further comprising a data processing means connected to said data recording means, said data processing means being for processing of data including data recorded by said data recording means.

6. The apparatus according to claim 2 further comprising a pressure sensing means connected to said separation vessel.

* * * * *